US009920362B2

United States Patent
Lai (10) Patent No.: US 9,920,362 B2
(45) Date of Patent: Mar. 20, 2018

(54) IDENTIFYING AND CORRECTING AN ALLELIC LADDER SIGNAL FOR DNA ANALYSIS

(75) Inventor: Ching Ming Lai, Wakefield, MA (US)

(73) Assignee: Analogic Corporation, Peabody, MA (US)

(*) Notice: Subject to any disclaimer, the term of this patent is extended or adjusted under 35 U.S.C. 154(b) by 435 days.

(21) Appl. No.: 13/977,316

(22) PCT Filed: Dec. 30, 2010

(86) PCT No.: PCT/US2010/062510
§ 371 (c)(1),
(2), (4) Date: Jun. 28, 2013

(87) PCT Pub. No.: WO2012/091717
PCT Pub. Date: Jul. 5, 2012

(65) Prior Publication Data
US 2013/0273529 A1    Oct. 17, 2013

(51) Int. Cl.
*C12Q 1/68*    (2018.01)
*G06F 19/24*    (2011.01)
*G06F 19/18*    (2011.01)
*G06F 19/16*    (2011.01)

(52) U.S. Cl.
CPC .......... *C12Q 1/6869* (2013.01); *G06F 19/24* (2013.01); *G06F 19/16* (2013.01); *G06F 19/18* (2013.01); *Y10T 436/143333* (2015.01)

(58) Field of Classification Search
CPC .................... G06F 19/00; G12Q 1/68
See application file for complete search history.

(56) References Cited

U.S. PATENT DOCUMENTS

| 5,599,666 A * | 2/1997 | Schumm et al. ............. 435/5 |
| 6,012,058 A * | 1/2000 | Fayyad ............ G06F 17/30705 |
| 6,028,190 A * | 2/2000 | Mathies ............. C12Q 1/6818 435/6.11 |
| 6,274,317 B1 | 8/2001 | Hiller et al. |
| 6,307,900 B1 * | 10/2001 | Choi ............. G11B 20/10009 375/262 |

(Continued)

FOREIGN PATENT DOCUMENTS

WO    WO2009156741 A1    12/2009

OTHER PUBLICATIONS

Dupuy et al. A dedicated internal standard in fragment length analysis of hyperpolymorphic short tandem repeats. Forensic Science International 86 : 207 (1997).*

(Continued)

*Primary Examiner* — G. Steven Vanni
(74) *Attorney, Agent, or Firm* — Anthony M. Del Zoppo, III; Driggs, Hogg, Daugherty & Del Zoppo, Co., LPA (57) ABSTRACT

A method for determining an allelic ladder signal for DNA analysis includes obtaining a measured allelic ladder signal for an allelic ladder substance, which includes a plurality of fragments, obtaining a reference set of expected fragment sizes of fragments of the ladder substance, and generating a signal identifying whether a peak for a fragment size of the measured ladder signal is a true peak of the ladder substance based on the reference set of expected fragment sizes, wherein the allelic ladder signal for DNA analysis includes the true peaks identified in the signal.

17 Claims, 4 Drawing Sheets

(56) References Cited

U.S. PATENT DOCUMENTS

| | | | |
|---|---|---|---|
| 6,531,282 B1 | 3/2003 | Dau et al. | |
| 6,750,011 B1* | 6/2004 | Perlin | G06F 19/18 435/6.11 |
| 6,991,713 B2 | 1/2006 | Adourian et al. | |
| 2002/0152035 A1* | 10/2002 | Perlin | 702/20 |
| 2003/0175701 A1* | 9/2003 | Griffiths et al. | 435/6 |
| 2004/0067494 A1* | 4/2004 | Wang | G06F 19/18 435/6.12 |
| 2004/0197925 A1* | 10/2004 | Gill | C12Q 1/6869 436/95 |
| 2005/0042668 A1* | 2/2005 | Perlin | 435/6 |
| 2006/0029975 A1* | 2/2006 | Barber | C12Q 1/6827 435/6.14 |
| 2007/0134706 A1* | 6/2007 | Matsumoto et al. | 435/6 |
| 2009/0228245 A1* | 9/2009 | Gilbert | G01N 30/8624 703/2 |
| 2009/0275038 A1* | 11/2009 | Hodge | 435/6 |
| 2013/0090861 A1* | 4/2013 | Lai | 702/20 |

OTHER PUBLICATIONS

Puers et al., Identification of Repeat Sequence Heterogeneity at the Polymorphic Short Tandem Repeat Locus HUMTHO I [AATG]n and Reassignment of Alleles in Population Analysis by Using a Locus-specific Allelic Ladder. American J. of Human Genetics 53 : 953 (1993).*

Smith, RN. Accurate size comparison of short tandem repeat alleles amplified by PCR. Biotechniques 18 (1) : 122 (1995).*

Butler et al., Application of dual internal standards for precise sizing of polymerase chain reaction products using capillary electrophoresis. Electrophoresis 16 : 974 (1995).*

Stoughton et al., Data-adaptive algorithms for calling alleles in repeat polymorphisms. Electrophoresis 18 : 1-5 (1997).*

Richards et al., Quantitative analysis of gel electrophoresis data for automated genotyping applications (Abstract). American J. of Human Genetics 57 (4 Suppl.) : A26 (1995).*

Zhang et al., Genetic Typing by Capillary Electrophoresis with the Allelic Ladder as an Absolute Standard. Analytical Chemistry 68 : 2927 (1996).*

Budowle et al., American J, of Human Genetics 48 :137 (1991).*

Ghosh et al., Methods for Precise Sizing, Automated Binning of Alleles, and Reduction of Error Rates in Large-Scale Genotyping Using Fluorescently Labeled Dinucleotide Markers. Genome Research 7: 165 (1997).*

Kimpton et al., PCR Methods and Applications 3:13 (1993).*

Margulies et al., Genome sequencing in microfabricated high-density picolitre reactors. Nature 437 :376 (2005).*

Ruitberg et al., STRBase: a short tandem repeat DNA database for the human identity testing community. Nucleic Acids Research 29(1) : 320 (2001).*

Zhang et al., Genetic Typing by Capillary Electrophoresis with the Allelic Ladder as an Absolute Standard . Analytical Chemistry 68: 2927(1996).*

Ziegle et al., Genomics 14 :1026 (1992).*

International search report for PCT/US2010/062510 published as WO. 2010/091717 A1.

J. M. Buttler, Forensic Data Typing Biology, Technology, and Genetics of STR Markers, 2005, pp. 688, Elsevier Academic Press, abstract attached 6 sheets.

* cited by examiner

IDENTIFYING AND CORRECTING AN ALLELIC LADDER SIGNAL FOR DNA ANALYSIS

RELATED APPLICATION

This application is a national filing of PCT application Serial No. PCT/US2010/062510, filed Dec. 30, 2010, published as WO 2012/091717 A1 on Jul. 5, 2012.

TECHNICAL FIELD

The following generally relates to DNA analysis and finds particular application to identifying and/or correcting an allelic ladder signal for DNA analysis.

BACKGROUND

DNA genotyping is a process of determining the sequence of DNA nucleotides at a generic locus, or at a position on a chromosome of a gene or other chromosome marker. For the purpose of identifying a human, certain generic loci have been selected as the standard markers to characterize the DNA. Each marker is a DNA fragment containing a repetition of a certain nucleotide sequence. Generally, there are thirteen (13) cores and several other accepted standard markers. These markers contain short repetitions (e.g., roughly from five (5) to forty (40)) of four (4) nucleotides. They are in the class of Short Tandem Repeat (STR) of DNA sequence.

The repetition numbers at these markers varies rather randomly from person to person. The specific form of DNA sequence at a generic locus is called an allele, which provides sufficient differentiation among people. The STR sequence is inherited from the parents DNA. At each marker, there may be two different alleles, one from each parent, and the marker is referred to as heterozygous. If the alleles from both parents have same STR numbers, the marker is referred to as homozygous. If the alleles of thirteen (13) core markers were heterozygous, each person would have twenty (26) different allele numbers. Assume each number is evenly distributed over a range of ten (10), the likelihood of having two people with the same alleles numbers from these thirteen (13) markers is extremely small.

To measure allele numbers, a DNA fragment containing all STR nucleotides and adjacent sections of nucleotides at each locus is copied from the DNA sample, and replicated by a technique called polymerase chain reaction (PCR). The fragment size is measured in the unit of base pairs, where a base pair is the size of a pair of DNA nucleotides. A substance containing synthesized fragments of known fragment sizes is added to the sample fluid. These added fragments are measured simultaneous with the DNA fragments. Because the sizes of these added fragments are known, they provide the means to calibrate for the DNA fragment sizes, and they have been referred to as internal sizing standards or internal lane standard (ILS) fragments.

A modern apparatus for DNA analysis uses a rigid sample carrier called biochip which contains multiple capillaries in parallel to run multiple samples simultaneously. The sample fluid is injected into one end of the capillary. The capillary has a negative electrode at injection end and positive electrode at other end. When a high voltage is applied to the electrodes, the electric field exerts a net electrostatic force on the surface charge of the fragment. The fragment moves or migrates toward the positive electrode at a speed depends on the electric field strength, the fragment size, and other factors. In this electrophoresis process, fragments of the same size arrives the positive electrode end at the same time, and they are separated from other fragments of different sizes.

The sizes of the fragments in a DNA locus are known to be within certain range. It is possible to find a number of loci in which the fragment sizes of a locus do not overlapped with other loci. Furthermore, it is possible to divide the whole set of loci into several groups. In each group, the fragment sizes of a locus are separated from other loci, and it is called a color group. For each color group, a dye with a distinct fluorescent color is attached to the fragments of all loci in the group. Usually, the dye is attached to a molecule called primer at one end of the fragment.

The fragments are separated by the electrophoresis process and detected by an optical system as a digital signal. A fragment is detected as a peak in the signal. The detection time (or the acquisition time) of peak can be used to determine the fragment size. Based on the non-overlapping range of the loci in the color group, the measured fragment size identifies the locus of the fragment. With other supporting data, the measured fragment size can be used to identify it as one of DNA fragments in the locus with known STR number.

The sample is prepared with multiple dyes with one dye for each color group. When the sample is excited by the light source, the fluorescent light is mixed with multiple colors from these dyes. It is necessary to use optical filter to separate the fluorescent colors. Each filtered fluorescent color is measured in a detection channel as an electrical signal. The strength of the signal is proportional to the amount of the fragments in the fluid. The ILS substance is labeled with a color different from the colors of the STR markers, such that the ILS signal can be separated from the signals of the markers.

To increase the measurement throughput, most of the apparatus is designed with capability to run multiple capillaries simultaneously, each containing a DNA sample of interest. These capillaries are packed into one biochip. Each capillary is referred to a "lane" or "sample channel" of the biochip. Advanced apparatus may use a biochip made of durable transparent glass or plastic and contain multiple capillaries with diameter as small as hundred (100) microns or less. The biochip is intended to be disposable, with one biochip used once only for one run.

In reality, the preparation and the environment of the sample fluid are not perfect. The migration speed of the fragments in the electrophoresis varies from one lane to another lane. It further varies from one run to another run. The migration times between fastest and slowest lanes can possibly differ by as much as a factor of two (2). As the result, the fragment sizes cannot be determined simply from the acquisition time of the peaks in the signal. The ILS substance contains only fragments of known sizes. These fragments migrate through the capillary under the same condition.

The acquisition times of the peaks in the ILS signal can be used as the scale to translate the acquisition time of a sample fragment into an ILS-translated fragment size. Unfortunately, the migration speed of a DNA fragment depends slightly on its nucleotide sequence and other factors. Consequently, the fragment size measured by the ILS signal (the ILS-translated fragment size) does not measure exactly the actual DNA fragment size, unless the DNA fragment happen to have the same nucleotide sequence as the ILS fragments.

To correct for this difference, a substance that contains virtually all possible DNA fragments of the markers is prepared and processed in a dedicated lane. The signal of this substance is called allelic ladder signal. The allelic ladder substance is prepared by combining genomic DNA or locus-specific PCR products from multiple people in a population. Each fragment in the ladder is considered a genuine DNA fragment, and its DNA fragment size is known and stays constant. The allelic ladder signal is detected like the DNA sample in multiple colors. Each peak in the allelic ladder signal indicates the expected peak position of a DNA fragment.

The ILS-translated fragment size for each of the ladder fragments is measured. Based on that, the allelic ladder signal provides a way to map a sample fragment from ILS-translated fragment size into actual DNA fragment size. In fact, for the allele number determination purpose here, the actual DNA fragment size is not important. The importance is the allele number of a DNA sample fragment. The allele number of every true ladder signal peak is known. Thus, the allelic ladder signal provides a way to map a sample fragment from ILS-translated fragment size into allele number or vice versus.

SUMMARY

Aspects of the application address the above matters, and others.

In one aspect, a method for determining an allelic ladder signal for DNA analysis includes obtaining a measured allelic ladder signal for an allelic ladder substance, which includes a plurality of fragments, obtaining a reference set of expected fragment sizes of fragments of the ladder substance, and generating a signal identifying whether a peak for a fragment size of the measured ladder signal is a true peak of the ladder substance based on the reference set of expected fragment sizes, wherein the allelic ladder signal for DNA analysis includes the true peaks identified in the signal.

In another aspect, a system a plurality of processing stations configured to concurrently process one or more DNA samples and an allelic ladder substance carried by different channels of a sample carrier, wherein the an internal lane sizing substance is include with both the DNA samples and the allelic ladder substance. The system further includes a reader that detects light emitted from fragments of the one or more DNA samples, the internal lane sizing substance and the allelic ladder substance in response to illuminating the fragments, and that generates one or more DNA signals, an internal lane sizing signal and an allelic ladder signal indicative of the detected light. The system further includes a translator that translates the one or more DNA signals from units of migration time to units of fragment size based on the internal lane sizing signal, and translates the ladder signals from units of migration time to units of fragment size based on the internal lane sizing signal. The system further includes a ladder signal corrector that corrects the translated allelic ladder signal. The corrected internal lane sizing translated ladder signal provides a mapping from allele numbers to internal lane sizing translated DNA fragment sizes in the internal lane sizing translated DNA signal.

In another aspect, a method includes determining allele numbers for ILS translated DNA fragment sizes of an ILS translated DNA signal using on a mapping of ILS fragment size to allele number that is based on a measured ILS translated allelic ladder signal, which is corrected by identifying and discarding false peaks and identifying and creating missing peaks so as to includes only a complete set of true allelic ladder substance peaks.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
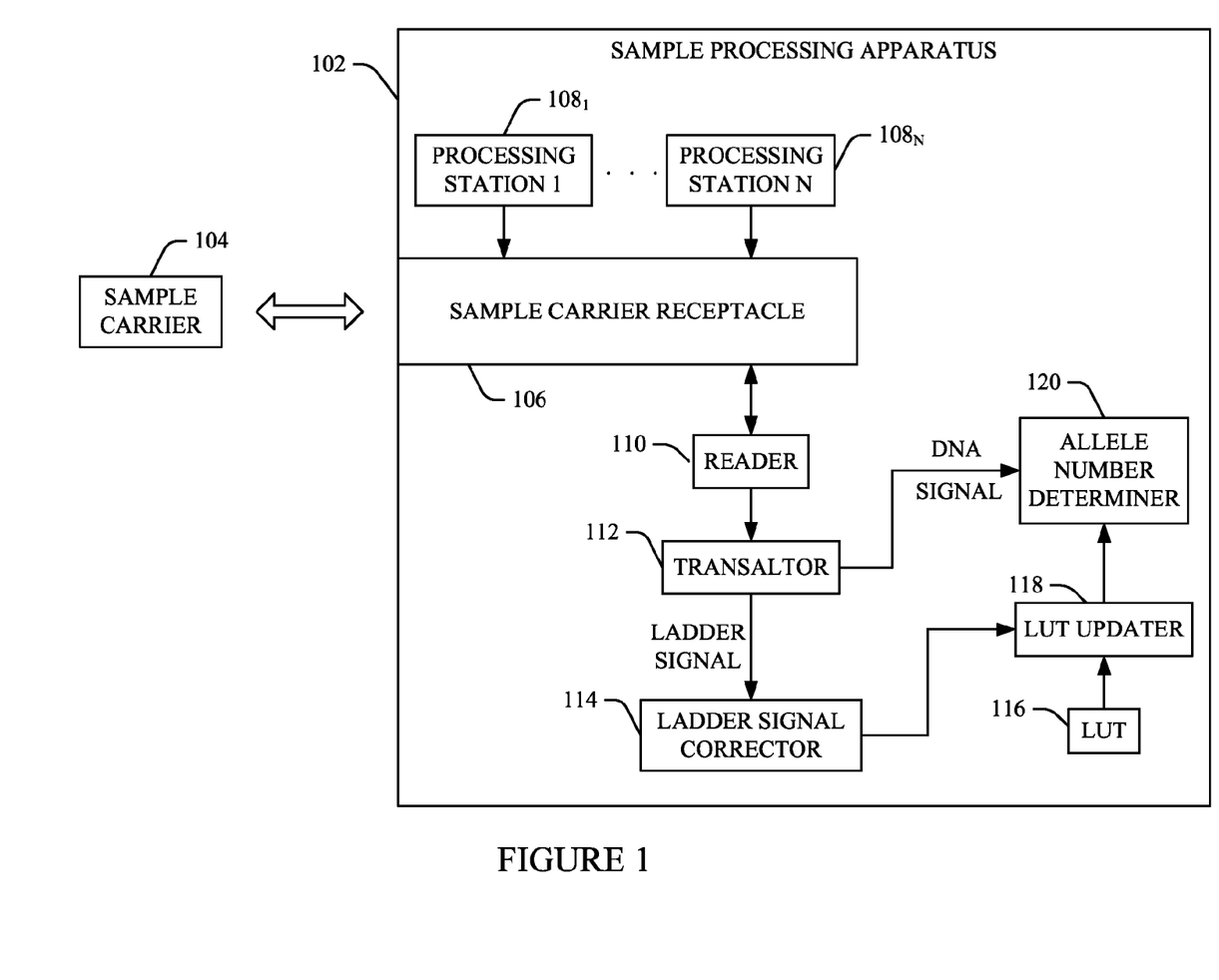
FIG. 1 schematically illustrates an example sample processing apparatus including a ladder signal corrector.

FIG. 1 illustrates a sample processing apparatus 102. The illustrated apparatus 102 is configured to process one or more samples carried by a sample carrier 104. A suitable sample carrier 104 includes, but is not limited to, a biochip, a lab-on-a-chip, and/or other sample carrier. Such a sample carrier 104 may include one or more micro-channels for carrying and moving, in parallel and/or in series, one or more samples through a plurality of different processing regions of the sample carrier 104.

Suitable samples include, but are not limited to, a bio-sample (e.g., saliva, blood, skin cells, and/or other bio-material), a non-bio sample, etc. With respect to DNA genotyping, the sample carrier 104 may carry one or more DNA samples (along with an internal lane standard (ILS) substance) respectively in one or more channels and a ladder substance (along with the ILS substance) in yet another channel. The sample processing apparatus 102 includes a sample carrier receptacle 106 configured to receive the sample carrier 104.

The sample processing apparatus 102 further includes one or more processing stations $108_1, \ldots, 108_N$, wherein N is an integer equal to or greater than one. The one or more processing stations $108_1, \ldots, 108_N$ are collectively referred to herein as processing stations 108. The illustrated sample processing apparatus 102 is configured to process samples carried by the sample carrier 104 and received by the sample carrier receptacle 106.

In one instance, such processing includes processing one or more DNA samples and the ladder substance carried by the sample carrier 104. In this instance, the processing stations 108 are configured to perform at least such functions as extract and purify fragments, replicate and label the fragments with fluorescent dyes having known emission spectrums (or colors), and separate the labeled fragments based on fragment size, for example, via electrophoresis.

The sample processing apparatus 102 also includes an optical reader 110. The reader 110 includes a light source that directs a light beam of a predetermined wavelength range at the separated DNA sample fragments and allelic ladder substance fragments. The reader 110 also includes a detector that detects light emitted by the dyes of the DNA sample, ILS substance, and allelic ladder substance fragments in response to the dyes receiving the light and generates an analog and/or digital signal indicative of the detected light for each of the DNA sample, the ILS substance, and the allelic ladder substance.

In one instance, the light source emits a relatively narrow light beam with a diameter in the order of ten (10) to one hundred (100) microns. In another instance, the light source emits a light beam with a smaller or large diameter. Examples of suitable light sources include, but are not limited to, a laser, a light emitting diode (LED), and the like. The reader 110 also includes an optical detection channel (e.g., a photo-multiplier tube (PMT), a charge-coupled device (CCD) camera, or the like) for each wavelength range (or color) of interest that generates an electrical signal in proportion to the intensity of the fluorescence light within the wavelength range.

A translator 112 receives the signals from the reader 110. The translator 112 translates the DNA fragment signal from units of acquisition (or migration) time to fragment size based on the ILS signal, producing ILS-translated DNA fragment sizes. The translator 112 also translates the allelic ladder signal from units of acquisition time to fragment size based on the ILS signal, producing ILS-translated allelic ladder fragment sizes.

A ladder signal corrector 114 corrects the ILS translated allelic ladder signal. As described in greater detail below, the ladder signal corrector 114 identifies true, false and/or missing peaks in the ILS translated allelic ladder signal, and generates a corrected ILS translated allelic ladder signal that includes a complete set of true peaks, in which every peak corresponds only to an ILS-translated fragment size of the allelic ladder substance. This may include discarding false peaks and/or creating peaks for missing peaks.

A look up table (LUT) 116 includes a set of predetermined fragment size-to-allele number mappings. A LUT updater 118 generates an updated LUT by updating the fragment size-to-allele number mappings in the LUT 116 based the corrected ILS translated allelic ladder signal. This includes updating the ILS translated fragment size of an allele in the LUT 116 to the corresponding ILS translated fragment size of the corrected ILS translated allelic ladder signal. For alleles in the LUT 116 that are not present in the corrected ILS translated allelic ladder signal, the ILS translated fragment sizes are interpolated from adjacent alleles.

An allele number determiner 120 determines DNA allele numbers for each peak in the DNA signal based on the ILS translated DNA fragment size and the updated look up table (LUT), which, as described above, includes a mapping that maps ILS translated fragment size to allele number. This can simply be done by using the mapping to determine an allele number based on an ILS translated DNA fragment size.

The translator 112, the corrector 114, the updater 118, and/or the determiner 120 can be implemented via one or more processors implementing one or more computer readable instructions encoded on computer readable storage medium such as physical memory. Additionally or alternatively, at least one of the one or more computer readable instructions can be carried by a carrier wave or signal. The LUT 116 and/or the allele numbers can be stored in computer readable medium.

Figure 2:
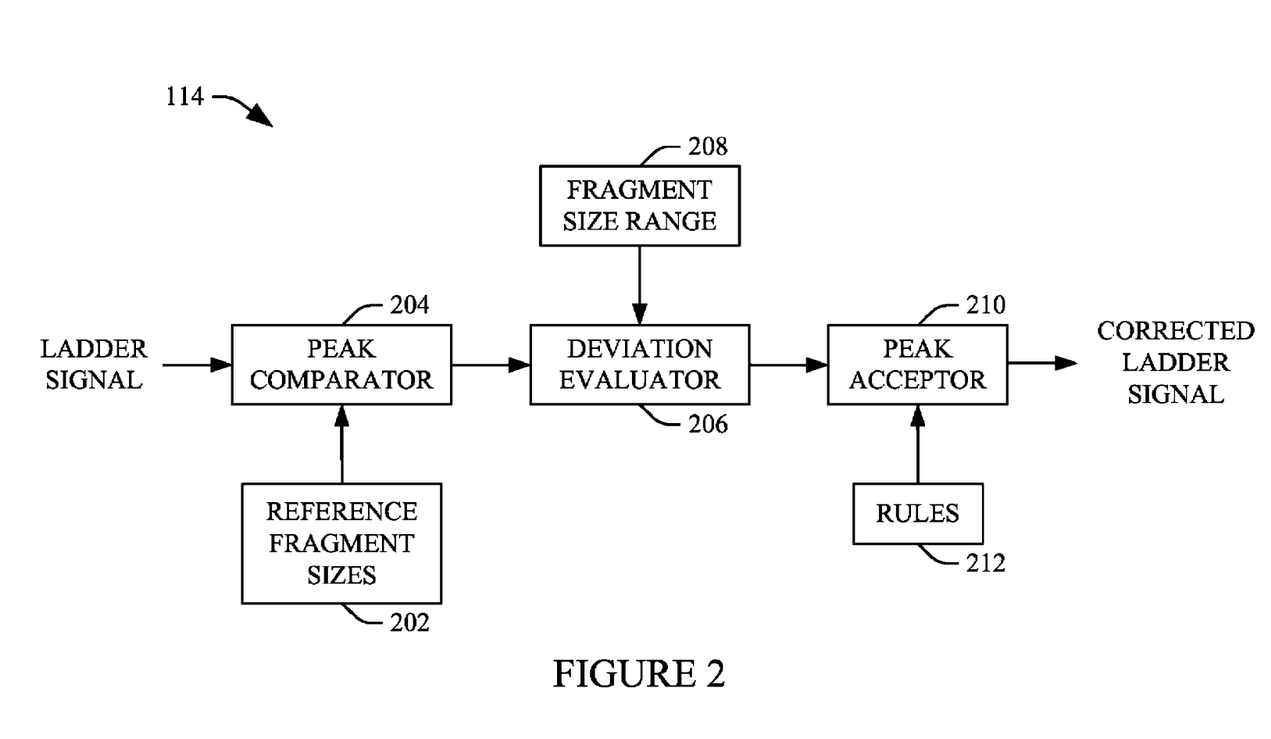
FIG. 2 schematically illustrates an example ladder signal corrector.

FIG. 2 illustrates an example of the ladder signal corrector 114.

A set of predetermined reference fragment sizes 202 includes reference ILS-translated fragment sizes for each peak of the allelic ladder substance. The reference fragment sizes 202 can be determined based on a set of empirical data and may include an average fragment size for every true peak in the ladder signal. The results obtained from each run can be used to update the average, and the average can be a weighted average, giving higher preference to more recent information. Generally, the reference fragment sizes 202 include a set of standard fragment sizes for the expected peaks in the ladder signal.

A peak comparator 204 compares each fragment sizes of the peaks in the allelic ladder signal with each of the reference fragment sizes in the reference fragment sizes 202 and generates a comparison signal or data indicative of the comparison. In one instance, this includes determining an absolute value of a difference between each fragment size of the peaks in the ladder signal and the reference fragment sizes in the reference fragment sizes 202.

A deviation evaluator 206 evaluates the comparison data based on a pre-determined fragment size range 208 and generates an evaluation signal or value indicative of the evaluation. In one instance, the evaluation value indicates whether a ladder signal fragment size is within the predetermined fragment size range 208 from a fragment size in the reference fragments sizes 202. The fragment size range 208 defines a valid range for every fragment size in the reference table.

Generally, if a peak in the allelic ladder signal is a true peak, the fragment size of the peak will fall within the predetermined fragment size range 208 of one of the fragment sizes in the reference fragment sizes 202. On the other hand, if the fragment size of a peak in the allelic ladder signal does not satisfy or fit into any fragment size range 208 around the fragment sizes in the reference fragment sizes 202, then the peak is considered a false peak.

A peak acceptor 210 accepts (and rejects) peaks in the ladder signal as true peaks based on the evaluation values and a pre-determined set of rules 212. By way of example, in one instance, if one or more fragment sizes of the ladder signal is within the fragment size range 208 from a reference fragments sizes 202, then the peak acceptor 210 acceptance the peak having the fragment size that is closest to the reference fragment size (i.e., the one with the smallest deviation) as the true peak.

The peak acceptor 210 rejects the other peaks corresponding to deviations satisfying the fragment size range 208 as false peaks. False peaks can be discarded, ignored, or otherwise removed from the allelic ladder signal. Where there is no peak with a fragment size within the fragment size range 208 from a reference fragment size in the fragment sizes 202, the peak is deemed missing, and the peak acceptor 210 generates a peak for the missing peak via interpolation or other means.

Optionally, in addition to the above, the ladder signal corrector 114 may first discriminate between true and false peaks in the ladder signal using known peak discrimination approaches. Examples of such approaches include, but are not limited to, measuring and testing against the peak shape, peak height, peak width, etc. The ladder signal corrector 114 removes peaks identified as false peaks.

Figure 3:
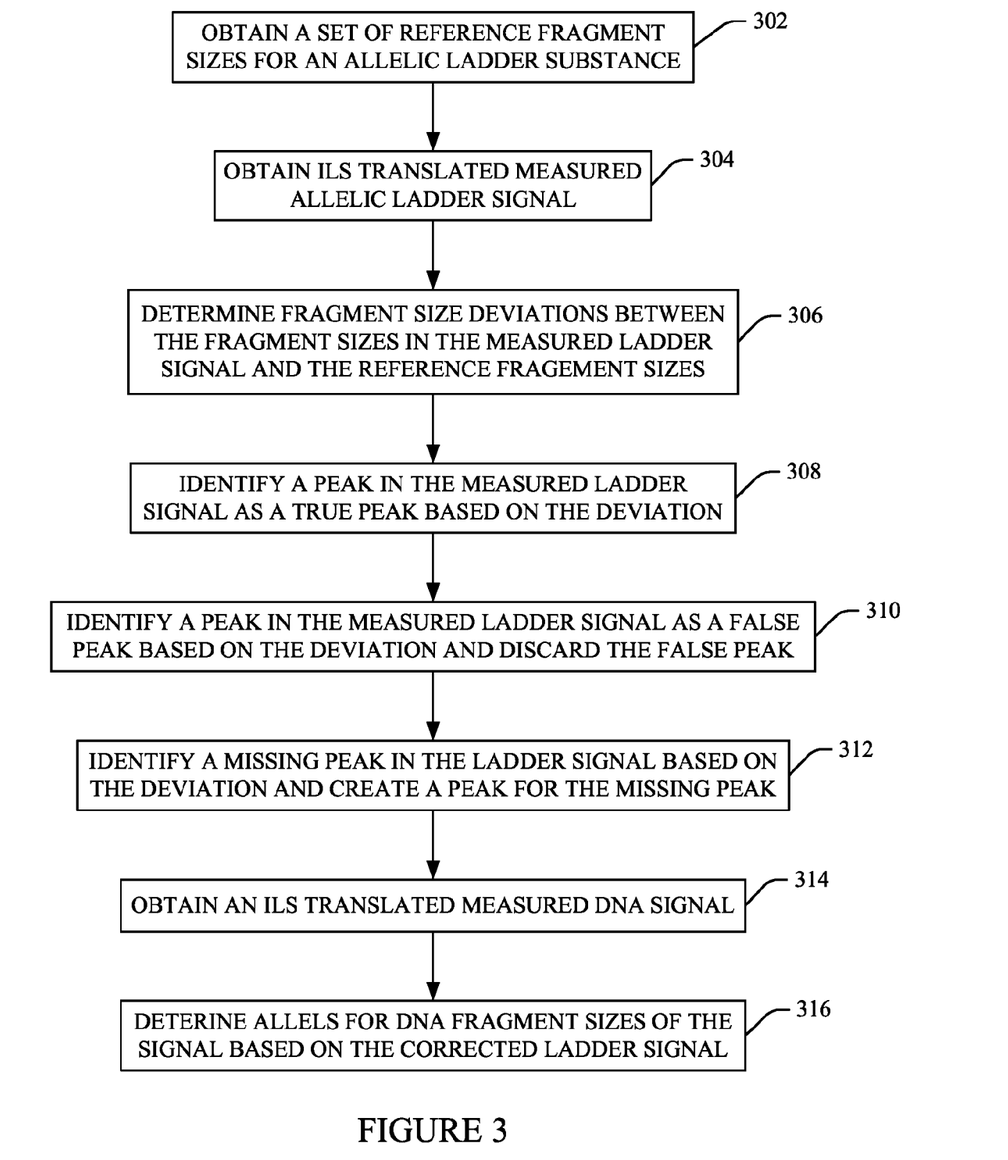
FIG. 3 illustrates a method for identifying and correcting the ladder signal.

FIG. 3 illustrates a method for determining the ladder signal for DNA analysis.

It is to be appreciated that the ordering of the following acts is not-limiting. As such, in other embodiments, the ordering may be different, and one or more acts may occur concurrently. In addition, one or more acts may be added and/or one or more of the acts may be omitted.

At 302, a reference set of ILS-translated fragments sizes for a ladder substance is obtained.

At 304, an ILS translated measured allelic ladder signal is obtained.

At 306, fragment size deviations between fragment sizes of the peaks of the measured ladder signal and peaks in the reference set are determined.

At 308, one or more true peaks are identified in the ladder signal. A peak in the ladder signal is identified as a true peak in response to the deviation for the peak being the smallest deviation from and satisfying the fragment size range 208 about a reference fragment size.

At 310, one or more false peaks are identified in the ladder signal and discarded. A peak in the ladder signal is identified as a false peak in response to the deviation for the peak not being the smallest deviation from and/or not satisfying the fragment size range 208 about the reference fragment size.

At 312, one or more missing peaks are created. Where the reference set of fragments sizes includes a fragment that does not correspond to a peak of the ladder signal, the peak is considered missing in the ladder signal and a peak is created in the ladder signal for the fragment size.

At 314, an ILS translated measured DNA signal is obtained.

At 316, allele numbers for the ILS translated DNA fragment sizes are determined based on the corrected ladder signal. As described herein, this includes using the corrected ladder signal to update a look up table that provides a mapping between allele number and fragment size, and then using the updated look up table to determine the allele number for an ILS translated DNA fragment size.

It is to be appreciated that the methods herein can be implemented via one or more processor of one or more computing systems executing one or more computer readable and/or executable instructions stored on computer storage medium such as memory local to or remote from the one or more computing systems.

The following provides another approach to describing the above. For this example, the ladder substance includes m fragments, the reference table includes m peaks with fragment sizes of $Q_1, Q_2, \ldots, Q_m$, and the measured ladder signal includes n peaks with fragment sizes of $P_1, P_2, \ldots, P_n$. To find the peak i of the reference table from the ladder signal, the deviation $D_i(j)$ between the fragment size of every peak in the ladder signal and $D_i(j)=|P_j-Q_i|$ for $j=1, 2, \ldots, n$.

Figure 4:
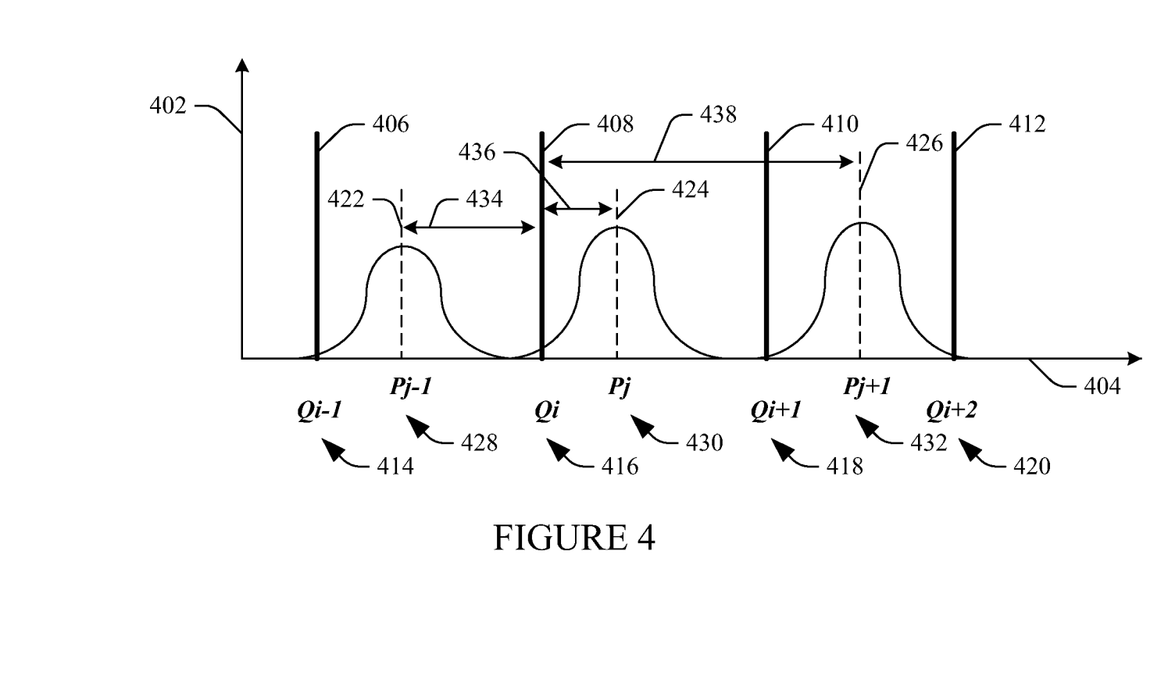
FIG. 4 graphically illustrates a portion of a ladder signal in connection with reference fragment sizes for the ladder signal.

FIG. 4 illustrated a sub-section of an example ladder signal in connection with reference fragments. In FIG. 4, a y-axis 402 represents signal amplitude and an x-axis 404 represents fragment size. Peaks 406, 408, 410 and 412 correspond to a sub-sets of fragments sizes 414 ($Q_{i-1}$), 416 ($Q_i$), 418 ($Q_{i+1}$), and 420 ($Q_{i+2}$) in the reference fragment sizes LUT 116. Peaks 422, 424 and 426 correspond to a sub-sets of fragments sizes 428 ($P_{j-1}$), 430 ($P_j$) and 432 ($P_{j+1}$) in the ladder signal. For fragment size 416 ($Q_i$), deviations 434 ($D_i(j-1)$), 436 ($D_i(j)$) and 438 ($D_i(j+1)$) respectively between the peak 408 and the peaks 422, 424 and 426 are illustrated.

If $D_i(k)$ is the one among these n values with minimal deviation and occurs at peak k of the ladder signal, and if $D_i(k)<D_{Limit}$ (where $D_{Limit}$ is the margin limit of the fragment-size deviation to qualify a peak as a peak in the reference table), then the ladder signal peak k is identified as the reference table peak i. Otherwise, the ladder signal peaks miss the reference table peak i.

After all peaks of the reference table have been tested, if a peak in the ladder signal is not identified as a peak in the reference table, then this peak is declared as a false peak. All the false peaks are removed from the list of peaks in the ladder signal. In the meantime, the missing peaks are created to fill the list of peaks for the ladder signal. This new list should have m peaks, including missing peaks with the fragment sizes to be interpolated. The new set of peaks is listed in the increasing order of fragment size as $P_1, P_2, \ldots, P_m$.

In the list, if $P_x$ is the fragment size of a missing peak with peak index of x, $P_x$ can be interpolated from the fragment sizes of adjacent peaks $P_{x-1}$ and $P_{x+1}$ with coefficient α as $P_x=P_{x-1}\alpha*(P_{x+1}-P_{x-1})$, which can be calculated as $P_x=P_{x-1}+(P_{x+1}-P_{x-1})*(Q_x-Q_{x-1})/(Q_{x+1}-Q_{x-1})$. The calculation uses the corresponding fragment size, $Q_x$, in the reference table to determine the interpolation coefficient $\alpha=(Q_x-Q_{x-1})/(Q_{x+1}-Q_{x-1})$. The above is a linear interpolation, and is sufficient. However, higher-order interpolations, such as quadratic or cubic interpolation, and other interpolation methods can alternatively be used.

The fragment sizes in the reference table (i.e. $Q_1, Q_2, \ldots, Q_m$) can be considered as the averaged fragment sizes from a number of ladder signals. The results obtained from the current ladder signal, i.e. the fragment sizes $P_1, P_2, \ldots, P_m$, can be used to improve the averaging process. In fact, the fragment sizes may drift slightly over a period of time due to slight changes in the instrument, in the sample preparation, and other reasons.

By including the results of the current ladder signal in calculating the averaged fragment sizes, the time-dependent drift also get corrected to some extent. In other words, the reference table is self-calibrated for the time-dependent drift by this practice. In this self-calibrated reference table, a weighting factor w is used for the averaging process.

The newly averaged fragment sizes become $Q'_i=(1.0-\omega)Q_i+\omega P_i$ with $0<\omega<<1$ and $i=1, 2, \ldots, m$. The weighting factor ω is substantially less than 1. The optimal ω value depends on the stability of the system and the frequency of running the samples. The reference table is then replaced by the fragment sizes, $Q'_1, Q'_2, \ldots, Q'_m$ calculated above. This self-calibration procedure is preferred but not necessary to use the basic method of this invention.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method for determining an allelic ladder signal for DNA analysis, comprising:

receiving a measured allelic ladder signal for an allelic ladder substance, which includes a plurality of fragments, wherein the measured allelic ladder signal is an electrical signal;

obtaining, from a memory device, a reference set of expected fragment sizes of fragments of the ladder substance;

comparing, with a processor, each fragment size of a peak of the measured allelic ladder signal with each of the expected fragment sizes to generate an electrical signal indicating of an absolute value of a difference between each of the fragment sizes of each of the peaks of the measured allelic ladder signal and each of the expected fragment sizes;

determining, with the processor and for each of the fragment sizes of the peaks of the allelic ladder signal, whether a fragment size of a peak of the peaks of the measured allelic ladder signal is within a predetermined fragment size range of each of the expected fragment sizes from the electrical signal indicating the absolute value;

identifying, with the processor and for each peak with a fragment size within the predetermined fragment size range of an expected fragment size, an expected fragment size closest to the fragment size of the peak from the electrical signal indicating the absolute value;

determining, with the processor, peaks with identified expected fragment sizes closest to the fragment sizes of the peaks as true peaks and all other peaks as false peaks; and generating, with the processor, the allelic ladder signal for DNA analysis with the true peaks and not the false peaks, wherein the allelic ladder signal for DNA analysis is an electrical signal.

2. The method of claim 1, wherein the false peaks are discarded from the measured allelic ladder signal.

3. The method of claim 1, further comprising:
determining the measured ladder signal is missing a peak.

4. The method of claim 3, further comprising:
generating a peak for the missing peak; and
including the generated peak in the allelic ladder signal for DNA analysis.

5. The method of claim 4, wherein generating the peak includes interpolating fragment sizes of neighboring peaks to generate the missing peak.

6. The method of claim 5, further comprising:
determining an interpolation coefficient used to interpolate the missing peak based on a corresponding fragment size in the reference set.

7. The method of claim 4, further comprising:
determining an allele number for a sample DNA fragment size based on the allelic ladder signal for DNA analysis.

8. The method of claim 7, wherein the sample DNA and the allelic ladder substance are concurrently processed in different lanes of a sample carrier.

9. The method of claim 1, wherein the reference set of expected fragment sizes of the fragments in the ladder includes an average of the fragment sizes from a plurality of ladder signals previously successfully verified.

10. The method of claim 9, further comprising:
updating the average based on a newly acquired and successfully verified ladder signal.

11. A method, comprising:
receiving, from an optical channel of an optical detector of an optical reader, a measured allelic ladder signal for an allelic ladder substance, which includes a plurality of fragments;
retrieving from a memory device a reference set of expected fragment sizes of fragments of the allelic ladder substance;
comparing, with a processor, each of the expected fragment sizes with each fragment sizes of each peak of the measured allelic ladder signal;
determining, with the processor, for a peak of the measured allelic ladder signal absolute values between a fragment size of each peak and each of the expected fragment sizes;

identifying, with the processor, and for the fragment, a first expected fragment size corresponding to a smallest deviation of the deviations for a peak;

comparing, with the processor, the smallest absolute value for each peak with a first predetermined threshold corresponding to the first expected fragment size;

identifying, with the processor, a peak as a true peak in response to the smallest absolute value for a peak satisfying the first predetermined threshold corresponding to the first expected fragment size;

identifying, with the processor, for each peak, a second expected fragment size corresponding to a second absolute value for each peak;

comparing, with the processor, the second absolute value for the each peak with a second predetermined threshold corresponding to the second expected fragment size;

identifying, with the processor and for a peak as a false peak in response to the second absolute value for a peak failing to satisfy the second predetermined threshold corresponding the second expected fragment size; and correcting the measured allelic ladder signal for DNA analysis by removing the false peak from the measured allelic ladder signal, which results in a corrected allelic ladder signal that includes only true peaks.

12. The method of claim 11, further comprising:
determining an allele number for a sample DNA fragment size with the corrected allelic ladder signal; and
sequencing the sample DNA with allele numbers determined for a plurality of DNA fragment sizes in the DNA sample.

13. The method of claim 11, further comprising:
identifying, with the processor, an expected fragment size with no identified true peak; and
creating, with the processor, a peak for the expected fragment size with no identified true peak by interpolating neighboring peaks using the expected fragment size as an interpolation coefficient,
wherein the corrected allelic ladder signal includes both true peaks and the interpolated peaks.

14. The method of claim 13, further comprising:
determining a new reference set of expected fragment sizes of fragments of the allelic ladder substance from the measured and corrected signal.

15. The method of claim 14, wherein the new reference set of expected fragment sizes of fragments of the allelic ladder substance includes an average fragment size for every true peak in the ladder signal.

16. The method of claim 15, further comprising:
updating the reference set and its average after each performance of the method over a plurality of performances.

17. The method of claim 15, wherein the average is a weighted average, with a first weight for a current run and a second weight for a previous run, and the first weight is greater than the second weight.

* * * * *